(12) United States Patent
Murali et al.

(10) Patent No.: US 11,666,229 B2
(45) Date of Patent: Jun. 6, 2023

(54) MONITORING DEVICE FOR MONITORING OF VITAL SIGNS (71) Applicant: SmartCardia SA, Lausanne (CH)

(72) Inventors: Srinivasan Murali, Lausanne (CH); Francisco Javier Rincon Vallejos, Renens (CH); Sébastien Baumann, Pully (CH); Ester Pérez Marcos, Renens (CH)

(73) Assignee: SmartCardia SA, Lausanne (CH)

( * ) Notice: Subject to any disclaimer, the term of this patent is extended or adjusted under 35 U.S.C. 154(b) by 375 days.

(21) Appl. No.: 16/766,617

(22) PCT Filed: Nov. 24, 2017

(86) PCT No.: PCT/IB2017/001446
§ 371 (c)(1),
(2) Date: May 22, 2020

(87) PCT Pub. No.: WO2019/102242
PCT Pub. Date: May 31, 2019

(65) Prior Publication Data
US 2021/0000351 A1  Jan. 7, 2021

(51) Int. Cl.
*A61B 5/389* (2021.01)
*A61B 5/00* (2006.01)
(Continued)

(52) U.S. Cl.
CPC ............ *A61B 5/02055* (2013.01); *A61B 5/25* (2021.01); *A61B 5/30* (2021.01); *A61B 5/389* (2021.01);
(Continued)

(58) Field of Classification Search
CPC ........ A61B 2560/04; A61B 2560/0468; A61B 2562/0204; A61B 2562/0217;
(Continued)

(56) References Cited

U.S. PATENT DOCUMENTS

| | | | |
|---|---|---|---|
| 5,919,141 A | 7/1999 | Money et al. | |
| 8,116,841 B2 | 2/2012 | Bly et al. | |

(Continued)

FOREIGN PATENT DOCUMENTS

| | | |
|---|---|---|
| EP | 2589333 A1 | 5/2013 |
| WO | 2009036616 A1 | 3/2009 |

(Continued)

OTHER PUBLICATIONS

Shiraishi, Naoto, and Yoshiyuki Sankai. "Pulse transit time measurement method with artifact tolerance for home healthcare." 2013 IEEE International Conference on Mechatronics and Automation. IEEE, 2013.

(Continued)

*Primary Examiner* — George Manuel
(74) *Attorney, Agent, or Firm* — Brooks Kushman P.C.

(57) ABSTRACT

A monitoring device for monitoring of vital signs of a living organism comprises at least two electrode pins for receiving an electrical activity of the living organism and an optical sensor for sensing a pulse of the living organism, wherein the monitoring device has a compact form and the at least two electrode pins and the optical sensor are integrated in the monitoring device.

8 Claims, 8 Drawing Sheets

(51) Int. Cl.
*A61B 5/0205* (2006.01)
*A61B 5/30* (2021.01)
*A61B 5/25* (2021.01)
*A61B 5/024* (2006.01)

(52) U.S. Cl.
CPC .......... *A61B 5/6823* (2013.01); *A61B 5/6824* (2013.01); *A61B 5/6833* (2013.01); *A61B 5/7203* (2013.01); *A61B 5/726* (2013.01); *A61B 5/7221* (2013.01); *A61B 5/02433* (2013.01); *A61B 2560/04* (2013.01); *A61B 2562/0204* (2013.01); *A61B 2562/0217* (2017.08); *A61B 2562/0219* (2013.01); *A61B 2562/0271* (2013.01); *A61B 2562/06* (2013.01)

(58) Field of Classification Search
CPC .... A61B 2562/0219; A61B 2562/0271; A61B 2562/06; A61B 2562/164; A61B 5/02055; A61B 5/02433; A61B 5/25; A61B 5/30; A61B 5/389; A61B 5/6823; A61B 5/6824; A61B 5/6832; A61B 5/6833; A61B 5/7203; A61B 5/7221; A61B 5/726
See application file for complete search history.

(56) References Cited

U.S. PATENT DOCUMENTS

| | | |
|---|---|---|
| 2007/0129633 A1* | 6/2007 | Lee .................. A61B 8/485 600/439 |
| 2008/0082004 A1 | 4/2008 | Banet et al. |
| 2014/0194761 A1 | 7/2014 | Lee et al. |
| 2014/0275932 A1 | 9/2014 | Zadig |
| 2017/0238833 A1 | 8/2017 | Felix et al. |

FOREIGN PATENT DOCUMENTS

| | | |
|---|---|---|
| WO | 2010107913 A2 | 9/2010 |
| WO | 2010107913 A3 | 1/2011 |

OTHER PUBLICATIONS

Sweeney, Kevin, Sean F. McLoone, and Tomas E. Ward. "A simple bio-signals quality measure for in-home monitoring." (2010).

* cited by examiner

MONITORING DEVICE FOR MONITORING OF VITAL SIGNS

CROSS-REFERENCE TO RELATED APPLICATIONS

This application is the U.S. National Phase of PCT/IB2017/001446 filed Nov. 24, 2017, the entire disclosures of which are incorporated by reference herein.

TECHNICAL FIELD

The disclosure relates to a monitoring device for monitoring of vital signs of a living organism. Furthermore, the disclosure relates to a carrying means, a method, a monitoring means, a computer program product, a computer-readable data carrier and a data carrier signal.

BACKGROUND

Accurately tracking vital signs of living organisms, such as the ElectroCardioGram (abbreviated ECG or EKG), pulse signal, oxygen saturation and arterial blood pressure is important to determine the health status and deterioration of such organisms, e. g. individuals and patients. In order to derive clinical insights, it's important to measure more than one vital sign simultaneously and to extract relevant information from these vital signs.

Wearable medical devices support non-intrusive and long-term monitoring of vital parameters of patients, such as electrocardiogram and pulse oximetry (SpO2). They represent new solutions in the healthcare domain, both for the prevention of acute episodes (e.g., strokes) and for the assessment of chronic conditions (e.g., sleep disorders, stress-related pathologies).

In general, monitoring vital signs is difficult to do on a continuous basis. Accurate measurement of cardiac pulse, for example, can be done using an ECG to detect the electrical activity of the heart. The ECG signal is a parameter that can be obtained by placing electrodes on the patient's body and it is one of the most used signals for non-invasive diagnosis of different cardiac diseases. An ECG is a test that can measure the electrical activity of the heartbeat. An ECG machine comes with one to ten electrodes (single lead to 12-lead ECG) placed at different points of the body to find the various signals associated with the cardiac function.

It is very difficult to obtain an ECG without noise. In particular, the ECG is often contaminated by the noise that can be within the frequency band of interest and can manifest with similar morphologies. Although each of these contaminants can be reduced by judicious use of hardware and experimental setup, it is impossible to remove all contaminants. Therefore, it is important to quantify the nature of the noise in a particular data set and it should be noted that the terms noise and artifact are often used interchangeably. Here, artifact is used to indicate the presence of a transient interruption (such as electrode motion) and noise is used to describe a persistent contaminant (such as mains interference).

Broadly speaking, ECG contaminants can be classified as:
Electrode pop or contact noise: Loss of contact between the electrode and the skin manifesting as sharp changes with saturation at FSD levels for periods of around 1 second on the ECG (usually due to an electrode being nearly or completely pulled off);
Electromyographic (EMG) noise: Electrical activity due to muscle contractions lasting around 50 ms between dc and 10,000 Hz with an average amplitude of 10% FSD level; and
Patient-electrode motion artifacts: Movement of the electrode away from the contact area on the skin, leading to variations in the impedance between the electrode and skin causing potential variations in the ECG and usually manifesting themselves as rapid (but continuous) baseline jumps or complete saturation for up to 0.5 second.

Although each of these contaminants can be reduced by judicious use of hardware and experimental setup, it is nearly impossible to remove all contaminants.

There is a strong need for ambulatory measurement of blood pressure (BP), as there is a growing number of hypertensive patients. Most devices for non-invasive measurement of blood pressure (NIBP) available are based on mechanical or oscillometric recordings and require a pressure cuff to be placed on the patient's upper arm or wrist. The periodic inflation of the cuff, usually every 20 minutes, is uncomfortable and noisy, disturbing the patient's sleep and interfering with the BP measures. As these devices require a gap of 2-3 minutes between subsequent recordings, they cannot be used to obtain continuous beat-to-beat recording of BP changes. It is, therefore, clear that there is a strong need for new NIBP methods to monitor, diagnose and follow-up patients at risk, as well as for healthy people for early diagnosis.

Several recent works have presented novel ways of measuring BP using different sensors. The most promising ones measure the pulse transit time (PTT) differences between different waveforms, such as the electrocardiogram (ECG), photo-plethysmogram (PPG), phonocardiogram (PCG), impedance cardiogram (ICG), electrical impedance tomography (EIT) or a combination of them.

Pulse sensing using Photoplethysmogram (PPG) sensing involves transmitting light waves at one or more wavelengths into the body of a living organism and detecting the pulsatile variations due to blood flow in the reflectance of the signals.

Arterial oxygen saturation (SaO2) level signifies the amount of oxygen-saturated hemoglobin relative to total hemoglobin in the blood. While SaO2 levels are typically obtained from testing blood samples, the peripheral oxygen saturation values (SpO2) are a good approximation of SaO2 values. A SpO2 sensor, typically used at the fingertip, transmits light at two different wavelengths (red and infrared range) and measures the absorption patterns at the two wavelengths. The SpO2 value is calculated in a ratio-metric manner, by measuring the dissimilar absorption coefficients to oxygenated and deoxygenated hemoglobin.

For measuring vital signs, a large variety of node placements has been proposed over the years, including wrist, upper arm, chest, hip, thigh, crus, ankle, and several combinations of them. However, not all the existing solutions aim at minimizing the patient's discomfort, often purposely increasing the number of sensors to collect a larger amount of data.

The measurement of temperature profiles on the human body surface provides several important insights for diagnosis and actionable insights. While the core body temperature is usually used for diagnosis of fever, the skin temperature also provides valuable information for diagnosis. The skin temperature can be measured at different peripheral points on the body, such as the armpit, upper arm, wrist or chest, among other locations.

In U.S. Pat. No. 5,919,141A, a vital sign remote monitoring device is disclosed. The device comprises of a plurality of sensors.

In US 20140275932, a disposable patch for vital signs monitoring is disclosed.

In U.S. Pat. No. 8,116,841 B2, an adherent device to measure ECG, respiration rate and other parameters is presented.

Conventional hospital systems measure multiple vital parameters using one or more devices placed at multiple locations of the human body. For example, the electrical activity of the heart (the Electrocardiogram or ECG) is measured using electrodes placed across the chest of the user. The pulse and peripheral oxygen saturation are measured using a finger clip attachment. The blood pressure is measured using an arm or wrist cuff, or using an arterial line. The muscle activity of the user is measured using Electro-MyoGram (EMG) device and electrodes placed at the location where the activity needs to be measured. In order to assess the complete health of an individual, it is important to measure and combine a variety of vital signs measurements. However, the available systems are typically complicated to install and to wear and typically comprise external cables, distributed components and the like.

In general, periodic monitoring of patients in a hospital is important to be sure that patients do not suffer an unnoticed sudden deterioration in their condition or a secondary injury during their stay in the hospital. It is impractical to provide continuous monitoring of a patient using sensors which are connected to a fixed monitoring system by wires. Furthermore, systems that sound an alarm when the measured value exceeds a threshold value may sound alarms so often and in situations that are not truly serious that such alarms are ignored by clinicians.

SUMMARY

It is the object of the disclosure to solve or to at least diminish the above-mentioned disadvantages. In particular, it is the objective of the disclosure to provide a solution for monitoring several vital signs of living organisms in a convenient manner.

This problem is solved by a monitoring device for monitoring of vital signs of a living organism, wherein the monitoring device comprises: at least two electrode pins for receiving an electrical activity of the living organism and an optical sensor for sensing a pulse of the living organism wherein the monitoring device has a compact form and the at least two electrode pins and the optical sensor are integrated in the monitoring device.

The expression "electrode pin" is to be understood as a connection point for an electrode. The expression "electrical activity" is to be understood as one or more electrical signal(s) created by the living organism, such as electrical signals created by heartbeats or electrical signals created by muscular activity or yet electrical signals created by brain activity. Such electrical signals can correspond to variations in potential differences. The expression "optical sensor" is to be understood as a generic term for an optical sensor arrangement, which could for example comprise a single photodetector or a multitude of photodetectors, possibly in combination with one or more light emitting diodes (LEDs). The expression "pulse" relates to a pulsatile blood flow, which is caused by a heartbeat, but a pulse rate measured at a certain location of the body is not the same thing as the heart rate measured directly at the heart. The expression "compact form" is to be understood such that the monitoring device is not a distributed device, e.g. a device formed by a multitude of freely accessible interconnected cables and/or sensors. The expression "integrated" is to be understood such that the electrode pins and the optical sensor are physically integrated in the compact form of the device and are not external components attached using loose cables or the like. The living organism can be a human being or yet an animal like a horse, a dog or a wild animal.

The disclosure solves the above-mentioned problem in a very advantageous manner, because the device can be attached to a particular part of the body of the living organism—for example the chest or the arm—and various vital signs can then be measured locally. The at least two electrode pins make it possible to attach electrodes to measure electrical activities of the body such as to derive an ECG therefrom and the optical sensor can be used to determine a PPG, and these two vital signs offer many possibilities for obtaining insights into the condition of the living organism. At the same time, the fact that the device is compact and has integrated components makes it easy to handle and comfortable to wear for the living organism.

In a typical embodiment, the monitoring device is configured to determine an Electrocardiogram (ECG) and/or an Electromyogram (EMG) by analyzing the electrical activity, wherein the electrical activity desirably comprises at least an ECG signal and/or at least an EMG signal. In particular embodiments, the monitoring device is configured to perform signal processing on the electrical activity received at the electrode pins such as to create an ECG and/or EMG that can be visualized on a screen or the like.

In a particular embodiment, the optical sensor is placed geometrically between the electrode pins and/or the monitoring device comprises at least one additional optical sensor. In typical embodiments, the optical sensor comprises a green LED and/or a red LED and/or an infra-red LED and one or more photodetectors. In typical embodiments, the optical sensor is configured to sense the pulse of the living organism using PPG sensing. In typical embodiments, the optical sensor is configured to be in contact with the skin of the living organism, either directly or with some optically clear layer in between.

In typical embodiments, the monitoring device essentially has the form of a rectangular cuboid, with maximum dimensions of 10 cm×6 cm×3 cm, typically with maximum dimensions of 7 cm×4 cm×2 cm, advantageously with maximum dimensions of 4 cm×2 cm×1 cm. Such a form and/or dimensions offer a good trade-off between space for components of the monitoring device and comfort for the living organism (also referred to as the user, wearer or patient) carrying the monitoring device. Alternatively, the monitoring device essentially has the form of a flat cylinder or a triangular cuboid or the like, desirably with similar dimensions as the ones mentioned above for the rectangular cuboid. In typical embodiments, the monitoring device has a maximum volume of 180 $cm^3$, typically a maximum volume of 56 $cm^3$, advantageously a maximum volume of 8 $cm^3$.

In typical embodiments, the electrode pins are located on one side of the monitoring device and the optical sensor is located on an opposite side of the monitoring device, wherein the electrode pins are configured to be connected to a carrying means. The expression "carrying means" is to be understood such that it refers to a device which is configured to carry the monitoring device and to be attached to the user. The advantage of such a configuration is that the monitoring device can be placed in such a way flat on the skin of a user that the optical sensor is in contact with the skin. This becomes possible because the electrode pins are located on the other side of the monitoring device, and it is thus not problematic if they protrude a bit from the monitoring device and/or that a connection between the electrode pins and electrodes, which link the electrode pins to the skin of the user, takes up some space. The closer the optical sensor is to the skin, the more precisely the PPG measurement can be carried out by the optical sensor.

In typical embodiments, the monitoring device comprises an accelerometer and/or a temperature sensor and/or a microphone and/or a vibration sensor and/or a gyroscope. The accelerometer has the advantage that it can be used to better analyze the electrical activity, for example for making a distinction between an ECG signal (based on heartbeats) or an EMG signal (based on muscular activity). The temperature sensor is typically configured to measure the skin temperature of the user and typically comprises a pad to be in contact with the skin. The temperature sensor is typically arranged on the same side of the device as the optical sensor, and a distance between the temperature sensor and the optical sensor is typically at least 5 mm, in particular at least 7 mm, advantageously at least 10 mm away from the optical sensor. Like this, interference between the two sensors is kept to a minimum and a close contact between the sensors and the user's skin is guaranteed.

In typical embodiments, the monitoring device comprises an electrical activity amplifier, wherein the electrical activity amplifier desirably comprises an ECG/EMG amplifier for amplifying the ECG signal and/or the EMG signal, an optical amplifier for amplifying at least one optical signal received by the optical sensor, a processor for receiving and processing the amplified signals, a memory to store the signals and/or processed information and a radio (e.g., a radio module) to communicate the signals and processed information to a mobile device. Like this, the mobile device can be used for visualizing the signals and processed information on its screen. For example, a smartphone as mobile device can be used for visualizing the ECG of the user.

A carrying means for carrying a monitoring device according to the disclosure is configured to be attached to a body of the living organism, for example using an adhesive product and/or a glue, wherein the carrying means is desirably configured to be attached to different parts of the body. Such body parts include for example chest, arm, wrist, leg, hip or back.

In typical embodiments, the carrying means comprises at least one, in some cases two, electrically conductive body connection line(s) configured to electrically connect the electrode pins to the body once the monitoring device is mounted in the carrying means, wherein the conductive body connection lines desirably comprise an electrically conducting material, such as stainless steel, and/or a hydrogel. In typical embodiments, each body connection line comprises an electrode contact pad, such that each body connection line connects one electrode pin of the monitoring device to one electrode contact pad once the monitoring device is mounted in the carrying means. In typical embodiments, at least one of the body connection lines comprises a conductive ink and/or a conductive tape. In typical embodiments, the body connection lines, in particular the electrode contact pads, are adapted to be attached to the skin of a living organism carrying the carrying means.

In typical embodiments, the carrying means is a disposable patch or a reusable band and desirably comprises a housing configured such that the monitoring device can be inserted into the housing, wherein the carrying means typically further comprises a flap configured to be opened and closed, wherein the flap is typically arranged in such a way on the carrying means that the flap faces the body when the carrying means is attached to the body. In typical embodiments, the patch is an adhesive patch which is desirably one-time disposable, to reduce bio-contamination of re-use. Alternatively, the patch is re-usable for longer term wear of the user. In another embodiment of the disclosure, the carrying means is or comprises a band that can be attached at the upper arm or wrist of a living organism. In typical embodiments, the patch is made of a foam material. In typical embodiments, the body connection lines and/or an electrode contact pad and or a line connection pin comprise(s) a conductive ink and/or a conductive tape.

In a typical embodiment, the body connection lines and/or the electrode contact pads are made of a conductive material such as stainless steel, carbon or another metal. Such body connection lines and/or electrode contact pads can be adhesive or non-adhesive. When they are non-adhesive, the carrying means can be secured to the user's skin using an additional adhesive tape or band, Typically, patches with gel electrodes are disposable, but carrying means with body connection lines and/or the electrode contact pads made from another material can be reusable. The monitoring device itself can be re-used across multiple patches and/or bands.

In typical embodiments, the flap comprises a first adhesive surface configured to stick to the monitoring device when the monitoring device is inserted in the housing and the flap is closed, wherein the flap advantageously comprises a second adhesive surface, configured to stick to the body when the carrying means is attached to the body. In typical embodiments, the first adhesive surface is configured to stick to that side of the monitoring device that comprises the optical sensor. In typical embodiments, the flap is a thin film with an adhesive material, e.g. a glue, applied to both its sides.

In typical embodiments, the flap comprises a view opening for the optical sensor and/or at least one additional opening. The view opening has the advantage of allowing a contact and/or interaction of the optical sensor with the skin of a wearer. However, if the flap is transparent this is typically the case in certain embodiments—such a view opening is not absolutely necessary. The additional opening can for example make it possible for a temperature sensor to get in contact with the skin.

A method for monitoring of vital signs of a living organism using a monitoring device comprises receiving an electrical activity of the living organism using at least two electrode pins and sensing a pulse of the living organism using an optical sensor. Therein, the monitoring device is typically a monitoring device according to any of the embodiments of the disclosure and/or the monitoring device is typically used in combination with a carrying means according to any of the embodiments of the disclosure.

In typical embodiments, the method comprises determining whether the electrical activity is a clean ECG signal or a combination of an ECG signal and an EMG signal. In such embodiments, the method does not necessarily comprise sensing a pulse of the living organism using the optical sensor.

In typical embodiments, the determining comprises measuring a time-dependent accelerometer waveform and a time-dependent waveform of the electrical activity simultaneously, computing the mean of the accelerometer waveform on a pre-defined time window, removing the mean from the accelerometer waveform over the time window so as to create a residual accelerometer signal, checking if a sum or a Root Mean Square (RMS) of the residual accelerometer signal exceeds a pre-defined signal threshold, and labeling the electrical activity as clean ECG signal if the sum or RMS does not exceed the pre-defined signal threshold and labeling the electrical activity as a combination of ECG and EMG signal if the sum or RMS exceeds the pre-defined signal threshold. In typical embodiments, the threshold is set experimentally. In one embodiment, the window size is set to 10 seconds. In typical embodiments, for calibrating, the sum or the RMS is computed when a particular person is walking at 4 km/h and the threshold is then set to this sum or RMS for this particular person.

In typical embodiments, the determining comprises measuring a time-dependent accelerometer waveform and a time-dependent waveform of the electrical activity simultaneously, computing the mean of the accelerometer waveform on a pre-defined time window, removing the mean from the accelerometer waveform over the time window so as to create a residual accelerometer signal, determining a power spectrum of the residual accelerometer signal, checking if a maximum amplitude of the power spectrum at any frequency exceeds a pre-defined power threshold and labeling the electrical activity as clean ECG signal if the power spectrum does not exceed the pre-defined power threshold and labeling the electrical activity as a combination of ECG and EMG signal if the power spectrum exceeds the pre-defined power threshold. The power spectrum of a signal decomposes the signal into multiple periodic signals at different frequencies. The maximum amplitude of any of the frequency components should be below the pre-defined threshold in the case of a clean ECG signal.

In typical embodiments, the determining comprises, if the electrical activity is labelled as a combination of ECG and EMG signal, transforming the accelerometer and electrical activity waveforms into frequency domains; removing the frequency components of the transformed accelerometer waveform from the frequency components of the electrical activity; re-constructing the electrical activity after removing the frequency components into time domain, with the resulting signal labelled as ECG signal; and subtracting the ECG signal from the original electrical activity and labelling the resulting signal as the EMG signal.

In typical embodiments, the determining comprises, if the electrical activity is labelled as a combination of ECG and EMG signal, transforming the accelerometer and electrical activity waveforms into wavelet domains; removing the wavelet components of the transformed accelerometer signal from the wavelet components of the electrical activity; re-constructing the electrical activity after removing the wavelet components into time domain, with the resulting signal labelled as ECG signal; and subtracting the ECG signal from the original electrical activity and labelling the resulting signal as the EMG signal.

In typical embodiments, the method comprises computing the heart rate in a rate time window from the electrical activity, computing the pulse rate from the pulse sensed by the optical sensor in the same rate time window, obtaining a position of the placement of the monitoring device on the body, wherein the position has one of the position values "arm" or "wrist" or "chest", discarding the electrical activity as noisy if the computed heart rate does not match the computed pulse rate and if the position of the monitoring device on the body has the position value "arm" or "wrist" and discarding the pulse as noisy if the computed heart rate does not match the computed pulse rate and if the position of the monitoring device on the body has the position value "chest".

In typical embodiments, the method comprises determining a Pulse Travel Time (PTT) based on the electrical activity and the pulse, and checking whether the PTT is noisy, wherein the PTT computed over a PTT-window of measurement is discarded as noisy if EMG is present and/or if the heart rate does not match to the pulse rate and/or if noise is present in either the ECG or the pulse.

In typical embodiments, the monitoring device according to any of the embodiments of the disclosure comprises a capability of performing each of the respective acts of the methods according the disclosure.

A monitoring means according to the disclosure comprises a monitoring device according to any of the embodiments of the disclosure and a carrying means according to any of the embodiments of the disclosure.

A computer program product according to the disclosure comprises instructions which, when the program is executed by a computer, cause the computer to carry out the method according to any of the embodiments of the disclosure.

A computer-readable data carrier according to the disclosure has stored thereon the computer program product according to the disclosure. Typical examples for such a computer-readable data carrier are memory sticks, DVDs or the like.

A data carrier signal according to the disclosure carries the computer program product according to the disclosure. A typical example for such a data carrier signal is a data stream related to a download of the computer program product over the internet.

BRIEF DESCRIPTION OF THE DRAWINGS

In the following, the disclosure is described in detail using a drawing, wherein shows.

DETAILED DESCRIPTION

Figure 1:
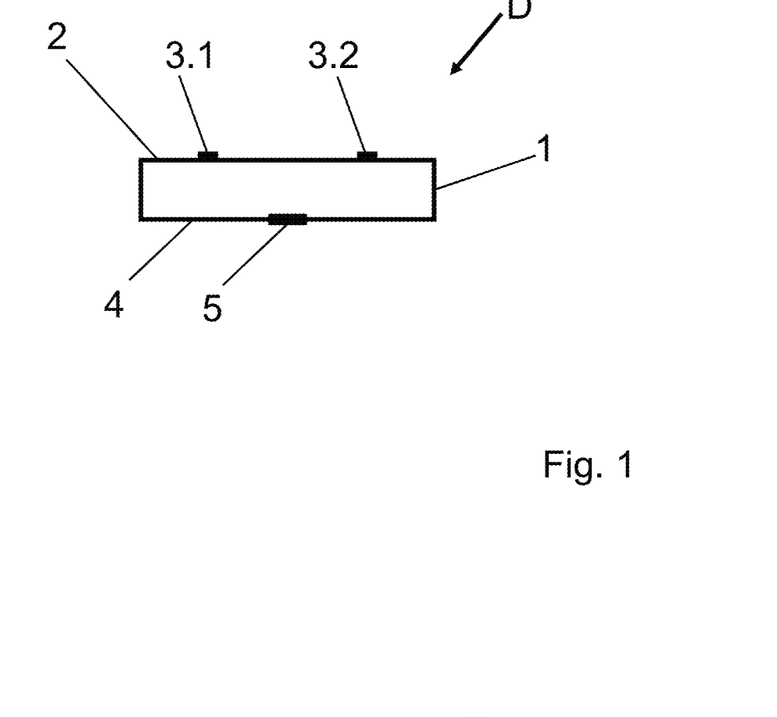
FIG. 1: a schematic side view of a monitoring device according to the disclosure.

FIG. 1 shows a schematic side view of a monitoring device D according to one embodiment of the disclosure. The monitoring device D comprises a casing 1, typically made from foam and/or plastic and/or metal. The monitoring device D comprises a front side 4 and a back side 2. Two electrode pins 3.1, 3.2 are integrated in the back side 2. These electrode pins 3.1, 3.2 are configured to be connected to body connection lines (not shown in FIG. 1) through which the monitoring device D can be electrically connected to the body of a living organism (not shown in FIG. 1) in order to measure an electrical activity (such as an ECG signal) of this living organism. The front side 4 of the monitoring device D comprises an optical sensor 5 for measuring the pulse of the living organism using PPG. For this, the optical sensor 5 comprises at least one light source and at least one photodetector (both not explicitly shown in FIG. 1). The optical sensor 5 is located geometrically between the two electrode pins 3.1, 3.2. In other words: a distance between the optical sensor 5 and the first electrode pin 3.1. is exactly the same as a distance between the optical sensor 5 and the second electrode pin 3.2.

The fact that the electrode pins 3.1, 3.2 and the optical sensors are arranged on opposite sides of the casing 1 has the advantage that body connection lines can be attached to the electrode pins 3.1, 3.2 without risking that the optical sensor 5 loses contact with a skin of the living organism (not shown) wearing the monitoring device D. In result, the PPG measurements carried out by the optical sensor 5 are highly precise and reliable.

Figure 2:
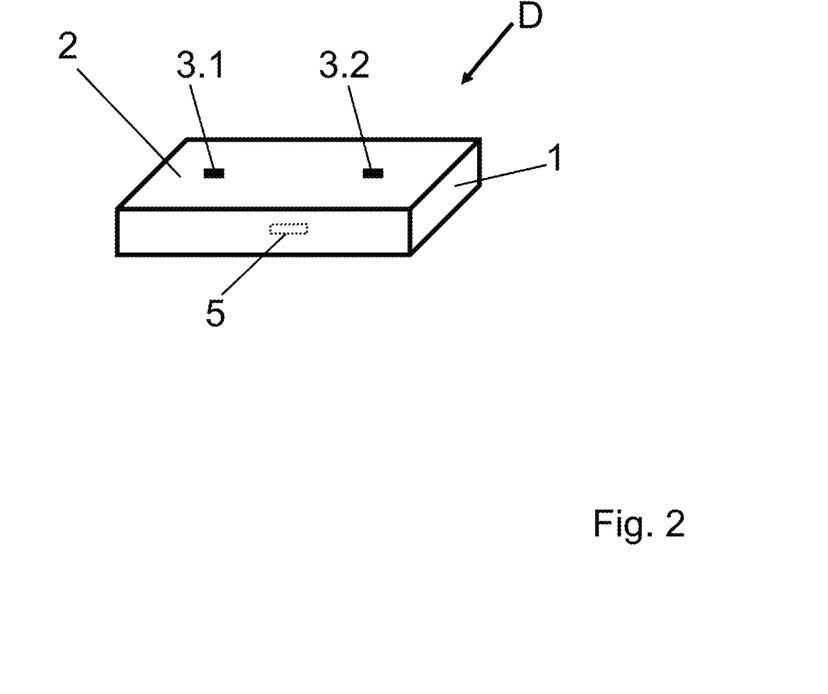
FIG. 2: a schematic perspective view of a monitoring device according to the disclosure.

FIG. 2 shows a schematic perspective view of the monitoring device D already shown in FIG. 1. It becomes very clear that the monitoring device D has the form of a rectangular cuboid and that the electrode pins 3.1, 3.2 on one hand and the optical sensor 5 on the other hand are located on opposite sides of the monitoring device D and/or the casing 1. The optical sensor 5 is indicated using a dotted line in FIG. 2 because the front side 4 on which it is arranged is not visible to the viewer in the perspective view shown in FIG. 2.

The monitoring device shown in FIGS. 1 and 2 typically houses further electronic components such as an electrical activity amplifier, wherein the electrical activity amplifier desirably comprises an ECG/EMG amplifier, an optical amplifier, a processor for receiving and processing the amplified signals, a memory for storing the signals and processed information and a radio module for communicating the signals and processed information to a mobile device. These electronic devices are not explicitly shown in FIGS. 1 and 2 for the sake of simplicity.

Figure 3:
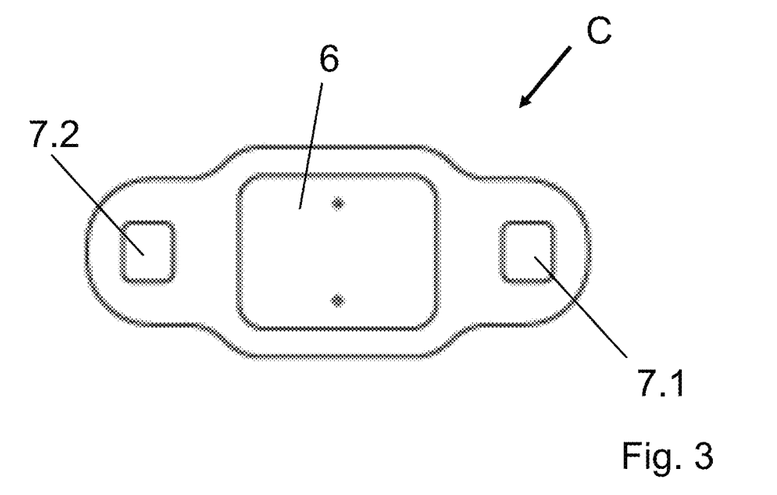
FIG. 3: a rear view of a carrying means according to the disclosure.

FIG. 3 shows a rear view of a carrying means C according to one embodiment of the disclosure. The carrying means C has the form of a patch. The carrying means C is typically made from plastic, is at least essentially waterproof and is configured to be attached to the skin of a living organism, much like a medical adhesive tape. In FIG. 3 is perceptible a rear side of a housing 6, integrated in the carrying means C. This housing 6 is configured to house the monitoring device D. By inserting and fixing the monitoring device D in the housing 6, a monitoring means according to the disclosure is created which can then be attached to the body of a living organism for monitoring the latter's vital signs (see FIG. 6). The carrying means C furthermore comprises two contact pad housings 7.1, 7.2 configured to accommodate electrode contact pads (not shown in FIG. 3) which are configured to establish an electrical connection with the skin of the living organism wearing the carrying means C. In the view of FIG. 3, the housing 6 and the contact pad housings 7.1, 7.2 form protuberances, but since the view of FIG. 3 is not a perspective view, this is not perceivable in FIG. 3.

Figure 4:
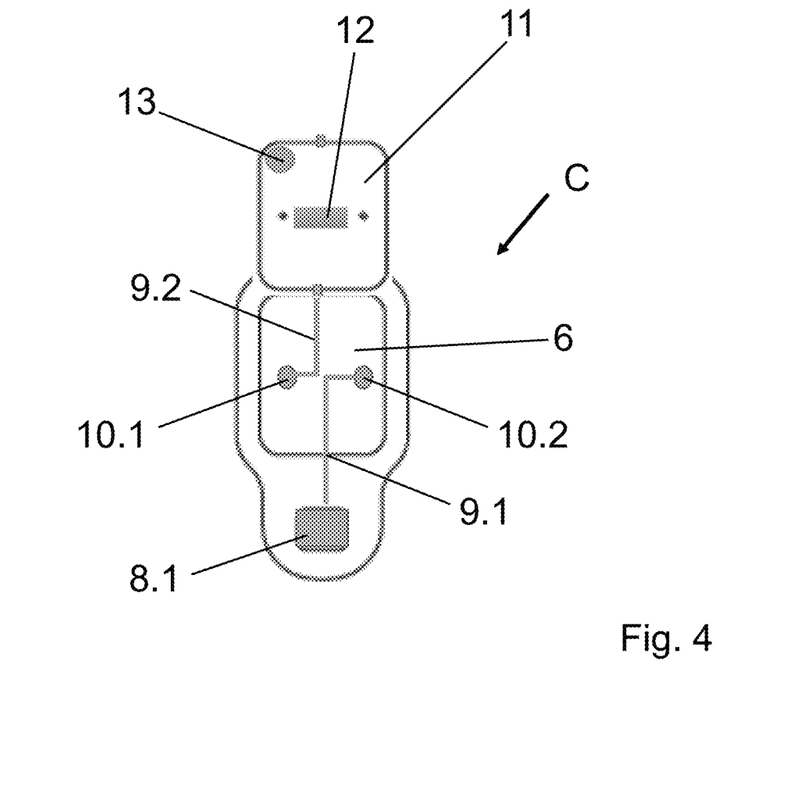
FIG. 4: a front view of a carrying means according to the disclosure (flap opened)

FIG. 4 shows a front view of the carrying means C already shown in FIG. 3. Yet again, the housing 6 can be perceived in FIG. 4. It forms a recess in FIG. 4 into which a monitoring device D according to the disclosure can be inserted. FIG. 4 furthermore shows a flap 11 of the carrying means C. Once the monitoring device D has been inserted into the housing 6, the flap 11 is typically closed to encapsulate the monitoring device D in the carrying means C. A back surface of the flap 11 (the back surface is the surface facing the viewer in FIG. 4) is typically coated with an adhesive product such that the flap 11 sticks to the monitoring device D once the flap 11 is closed. Also a front surface of the flap 11 (the front surface is the surface pointing away from the viewer in FIG. 4) is typically coated with an adhesive product such as to stick the flap 11 to the skin of a living organism carrying the carrying means C. The entire front surface of the carrying means C (this is the surface of the carrying means C facing the viewer in FIG. 4) is typically also coated with an adhesive product. Like this, the carrying means C as a whole can be attached to the skin of a living organism.

FIG. 4 furthermore shows that the carrying means C comprises two line connection pins 10.1, 10.2. These line connection pins 10.1, 10.2 are configured to be attached to the electrode pins of a monitoring device D according to the disclosure (not shown in FIG. 4). In typical embodiments, the line connection pins 10.1, 10.2 have the form of female fastener buttons and the electrode pins have the form of male fastener buttons, or vice-versa. The line connection pins 10.1, 10.2 are connected to respective body connection lines 9.1, 9.2 which are themselves integrated in the carrying means C and which are connected to respective electrode contact pads 8.1, 8.2. In FIG. 4, only a first electrode contact pad 8.1 is perceivable; a second electrode contact pad 8.2 is hidden by the opened flap 11 in FIG. 4. The flap 11 furthermore comprises a view opening 12 for the optical sensor of the monitoring device D and an additional opening 13, which can serve for example for allowing a temperature sensor of a monitoring device D mounted in the housing 6 to touch the skin of a living organism wearing the monitoring means.

Figure 5:
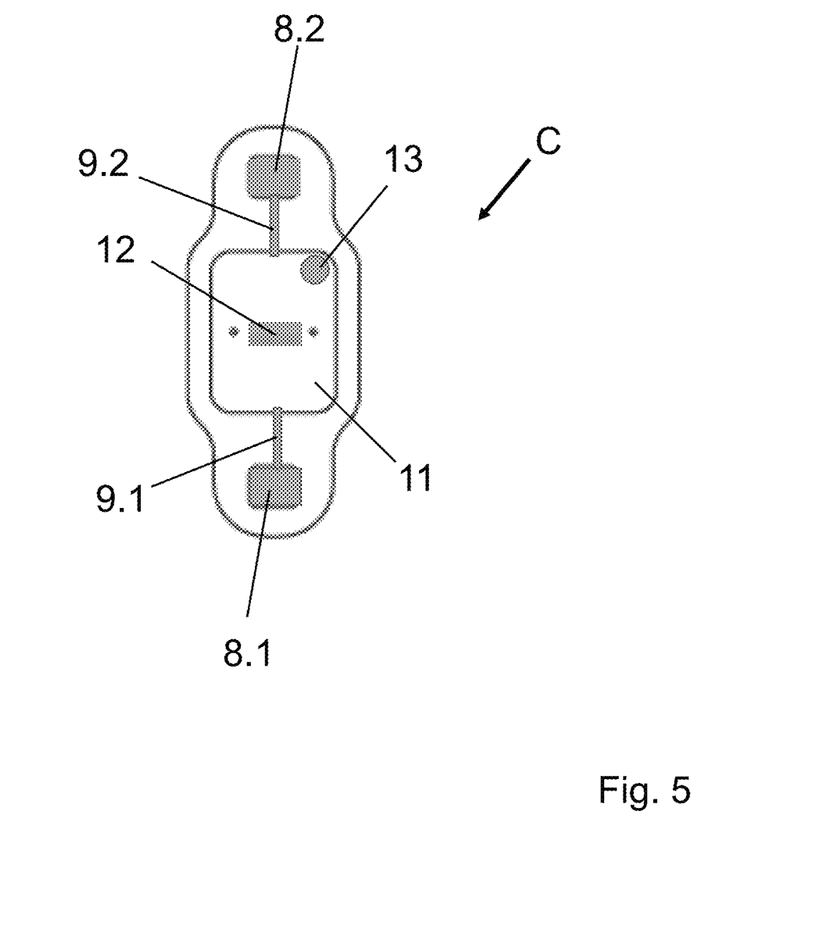
FIG. 5: a front view of a carrying means according to the disclosure (flap closed)

FIG. 5 also shows a front view of the carrying means C already shown in FIGS. 3 and 4, but this time the flap 11 is closed. Therefore, also the second electrode contact pad 8.2 is perceivable in FIG. 5. For the other features shown in FIG. 5, reference is made to the above description of FIG. 4. It is pointed out that the components of the carrying means C shown in FIG. 5 are not visible when the carrying means is worn by a living organism because they are in contact with the skin of this living organism. What is visible when the carrying means is worn is the view visualized in FIG. 3.

Figure 6:
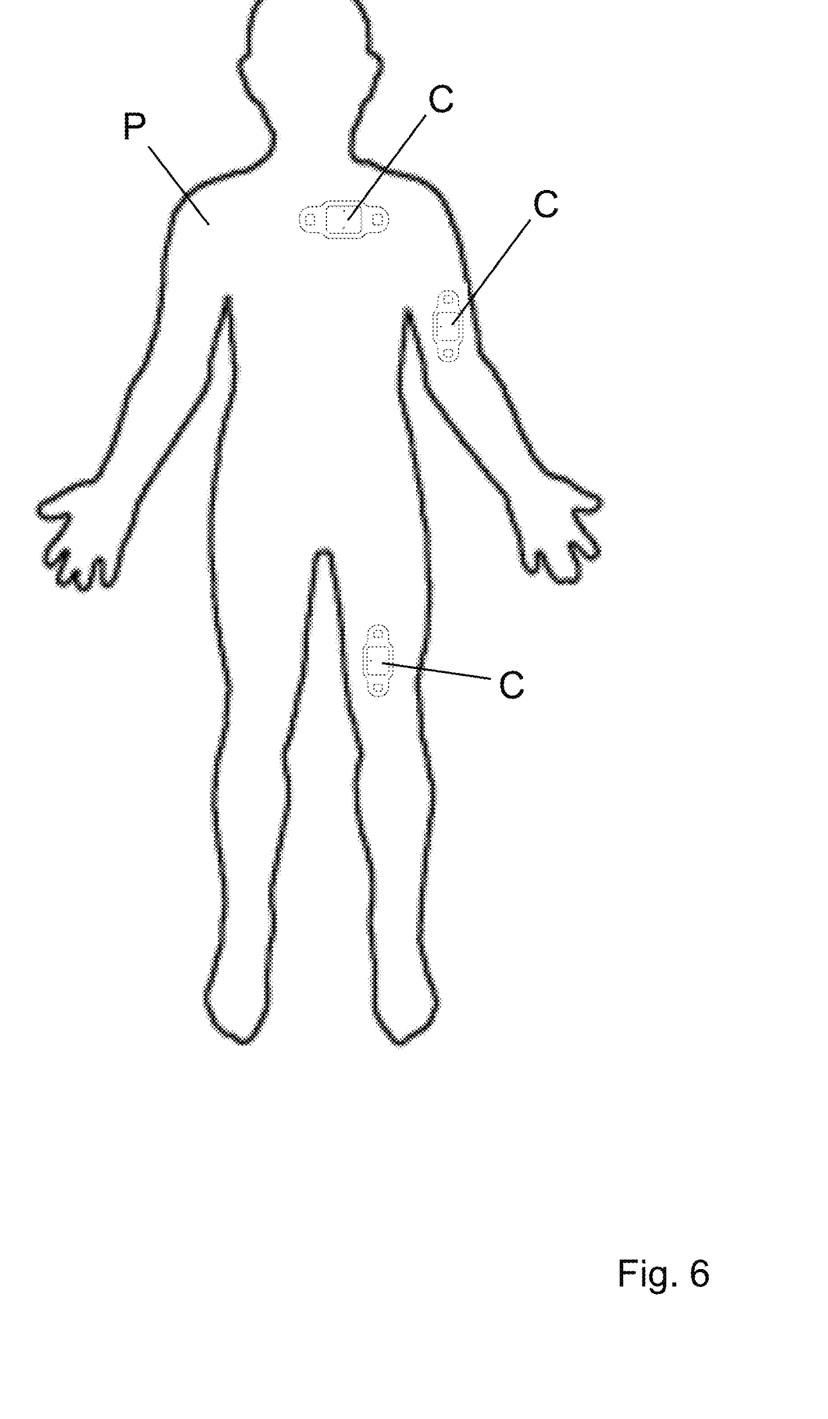
FIG. 6: a patient wearing three carrying means according to the disclosure.

FIG. 6 shows a patient P wearing three carrying means C according to one embodiment of the disclosure. The carrying means C have the form of patches and correspond to the patches shown in FIGS. 3, 4 and 5. The carrying means C each comprise one monitoring device D (not perceivable in FIG. 6) and thus each form a monitoring means according to the disclosure, together with the respective monitoring device D that they are each carrying. It can be observed in FIG. 6 that the carrying means C in the form of patches can be worn at different body parts of the patient P, namely the chest, the arm and the leg. Wearing the patches at other body parts is also possible. Furthermore, it can be observed that it is possible to wear the patches horizontally (as shown for the patch attached to the chest) and also vertically (as for the patches on the arm and the leg).

Figure 7:
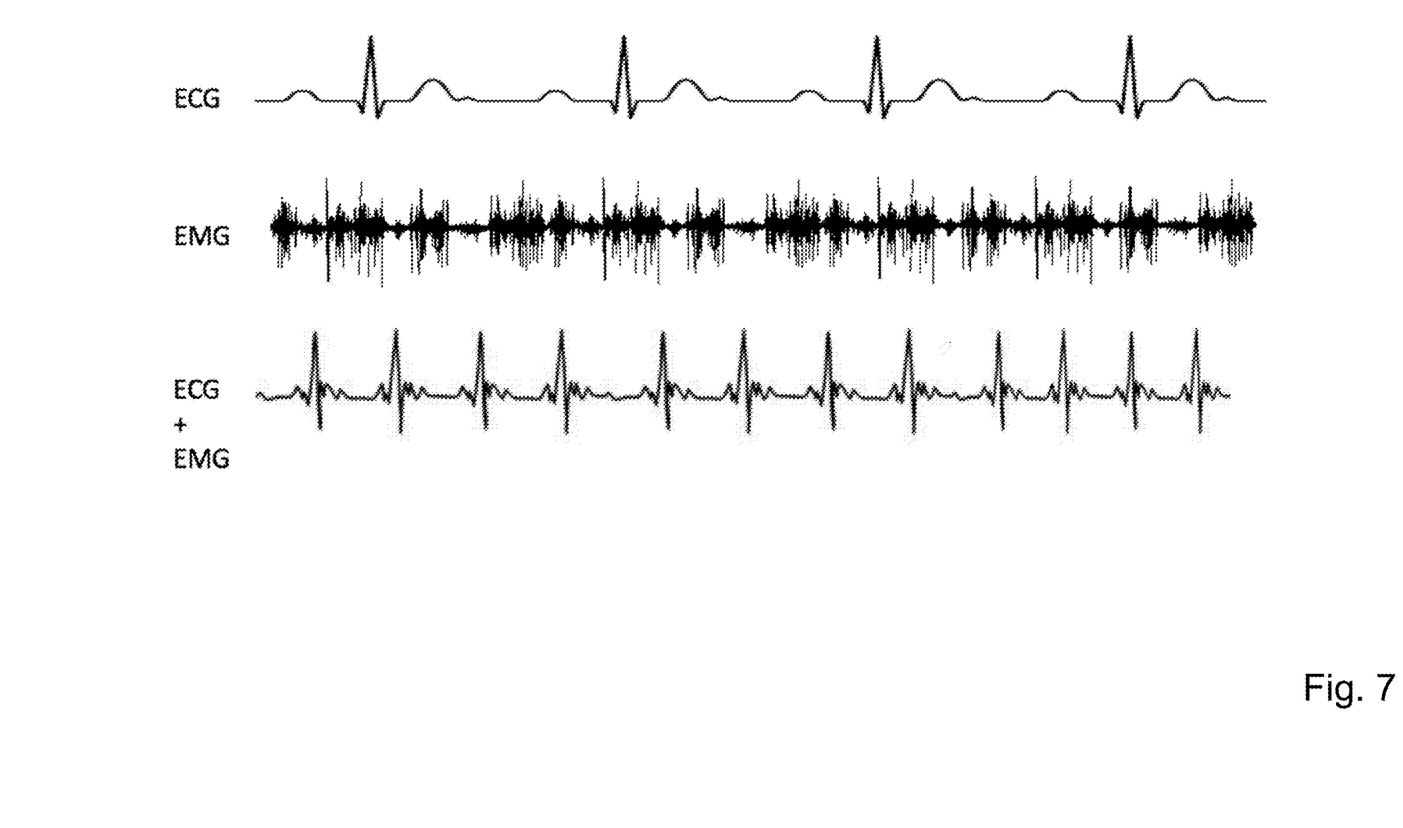
FIG. 7: electrical activities of a living organism, namely an ECG signal, an EMG signal and a combined ECG/EMG signal.

FIG. 7 shows types of electrical activities that can typically be received by a monitoring device D according to the disclosure. In particular, FIG. 7 shows as examples for the electrical activity of a body of a living organism—an ECG signal (top), an EMG signal (middle) and a combined ECG/EMG-signal. The combined ECG/EMG-signal is typically received, when muscular activity interferes with the measurement of an ECG-signal, for example because a patient is moving a part of his body or is experiencing twitches or the like. In these cases, the EMG component in the ECG/EMG-signal can be considered as noise. In a particular method according to the disclosure, an electrical activity of a living organism is received and it is then determined whether the electrical activity is a clean ECG signal or a combination of an ECG signal and an EMG signal (or in other words: an ECG/EMG-signal). Thereafter, the EMG component is removed from the ECG/EMG-signal in order to obtain a clean ECG-signal.

In one typical method according to the disclosure, the determination whether the electrical activity is a clean ECG signal or an ECG/EMG-signal is carried out as follows: A time-dependent accelerometer waveform and a time-dependent waveform of the electrical activity is measured simultaneously. The mean of the accelerometer waveform is computed on a pre-defined time window. Then, the mean is removed from the accelerometer waveform over the time window. Then, it is checked if a power spectrum of the accelerometer waveform after removing the mean over the time window exceeds a pre-defined power threshold. The electrical activity is labelled as clean ECG-signal if the power spectrum does not exceed the pre-defined power threshold and is labelled as a combination of ECG and EMG signal if the power spectrum exceeds the pre-defined power threshold. To carry out this type of determination, a monitoring device comprising at least a capability to receive and to analyze the electrical activity and furthermore comprising an accelerometer is typically used.

In the case where it has been determined that the electrical activity is ECG/EMG-signal, the EMG component needs to be removed from the ECG/EMG-signal in order to obtain the desired clean ECG-signal. In a typical method according to the disclosure, this is done as follows: If the electrical activity has been labelled as a combination of ECG and EMG signal, the accelerometer waveform and the electrical activity waveform are transformed into frequency domains. Then, the frequency components of the transformed accelerometer waveform are removed from the frequency components of the electrical activity. Then, the electrical activity is re-constructed—after having removed the frequency components of the transformed accelerometer waveform into the time domain, with the resulting signal being labelled as ECG-signal. Then, this ECG-signal is subtracted from the original electrical activity, and the resulting signal is labelled as the EMG-signal.

In typical embodiments of the disclosure, a method for monitoring of vital signs of a living organism using a monitoring device comprises analyzing a pulse transit time (abbreviated "PTT"). The PTT represents the time needed by a pulse wave to exit the heart and reach a PPG measurement site (for example a part of the body where the optical sensor of a monitoring device according to the disclosure is located). In addition, one should know that the bigger the distance between that PPG measurement site and the heart is, the less impact mistaken measurement values (in the time domain) has on the PTT determination. A monitoring means according to the disclosure, typically a patch, typically measures the PTT, which is a marker for blood pressure variations. It can be used for tracking long term BP variations.

It takes two sensors to measure the PTT: an ECG sensor (that is, for example a monitoring device according to the disclosure) and a PPG sensor. These two sensors make it possible to know when the pulse has left the heart and when it arrives for example at the upper arm or the chest area (which are typical locations for a capability to make a measurement).

The blood pressure measurement starts when the measurement device (e.g. a patch or armband) is placed on the body and the ECG sensor comes into contact with the body's skin—for example using the before-mentioned electrode contact pads. A one-lead ECG rhythm begins recording and each large spike on the ECG signals a contraction of the heart—this is approximately when a pulse leaves the heart. From the heart, this pulse travels out to the peripheral parts of the body, such as an upper arm, where it will meet the PPG sensor on the front side of the patch (if a patch is attached to the upper arm)—this creates a peak in the PPG waveform. In typical embodiments of the disclosure, the PTT is measured as the time between the peaks of the ECG and PPG waveform, which is how long it took for a pulse to travel from the heart to the upper arm. The PTT can also be measured as the time difference from other characteristic points on the ECG waveform to characteristic points on the PPG waveform (such as the foot of the PPG).

Since PTT can be estimated from the measured ECG and PPG, said patch or armband is very useful to measure the blood pressure (abbreviated "BP") continuously and conveniently.

In a typical embodiment of the disclosure, the PTT computed over a window of measurement is discarded as noisy if significant EMG is present.

In a typical embodiment of a method according to the disclosure, the PTT computed over a window of measurement is discarded as noisy if the heart rate derived from the ECG does not match the pulse rate derived from the pulse sensor, in particular the optical sensor used for creating a PPG, in the window.

In a typical embodiment of a method according to the disclosure, the PTT computed over a window of measurement is discarded as noisy if significant noise is present in either the ECG or pulse signals.

In a typical embodiment of a method according to the disclosure, the exact location where the monitoring device is placed is taken as an input parameter for the method. This is advantageous because the PTT values depend on the exact location where the monitoring device is placed. In a typical embodiment of a method according to the disclosure, depending on the user's height, the distance from the chest to the arm is taken as an input parameter for the method. This is advantageous because this distance changes from user to user and considering it will make the method more precise.

In a typical embodiment of a method according to the disclosure, the user's height and the location of placement of the monitoring device are obtained as an input, and depending on the location and height, the computed PTT values are normalized. For example, a simple normalization co-efficient is obtained using the following method: A user will wear two monitoring devices simultaneously, at chest and upper arm. The computed PTT values from both these locations are then fitted with the height of the user using a linear fit. This normalization equation or co-efficient is then used to translate the PTT to a standard value based on the location of placement of the device.

Figure 8:
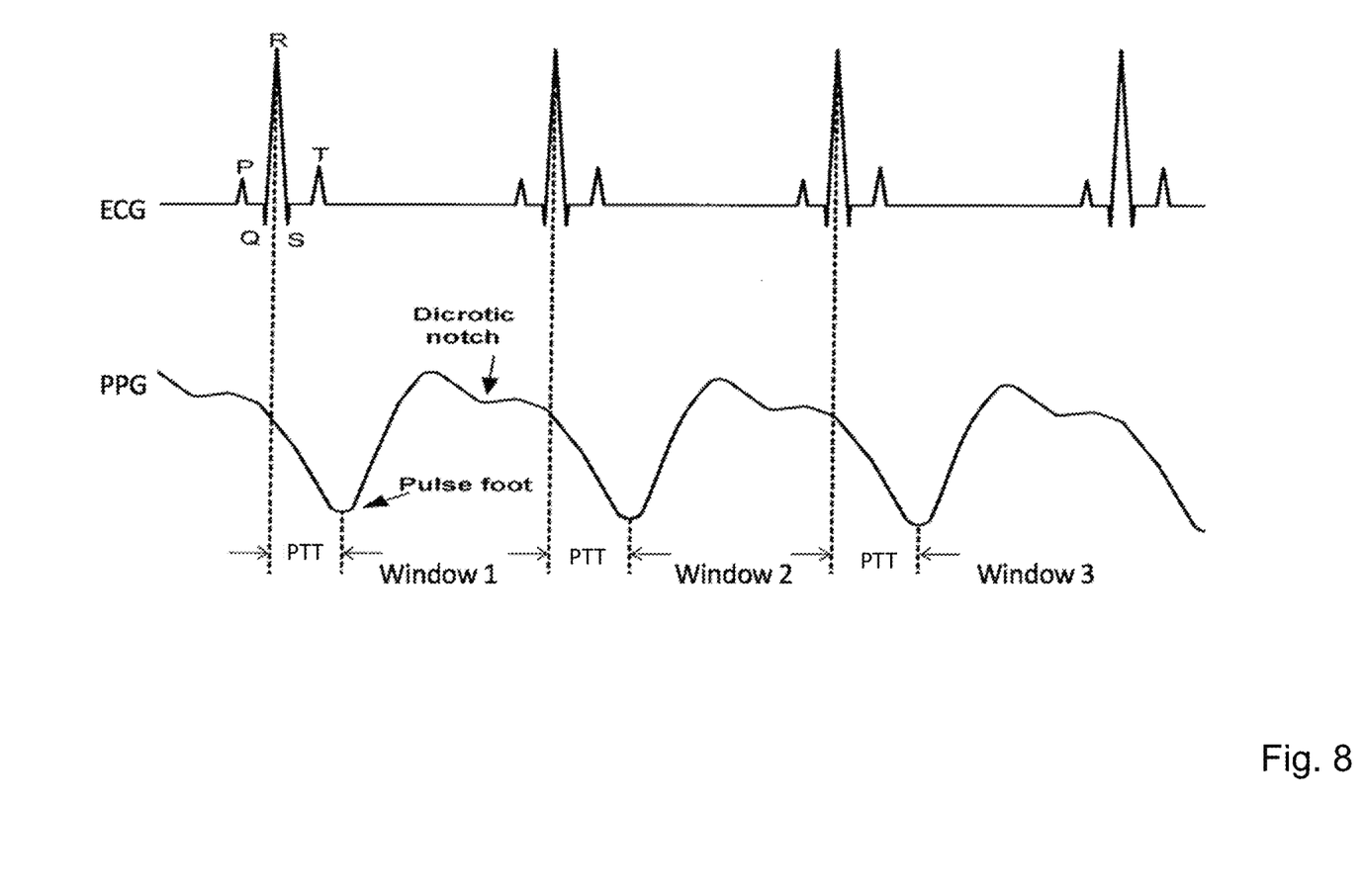
FIG. 8: an ECG signal and a PPG curve.
Figure 9:
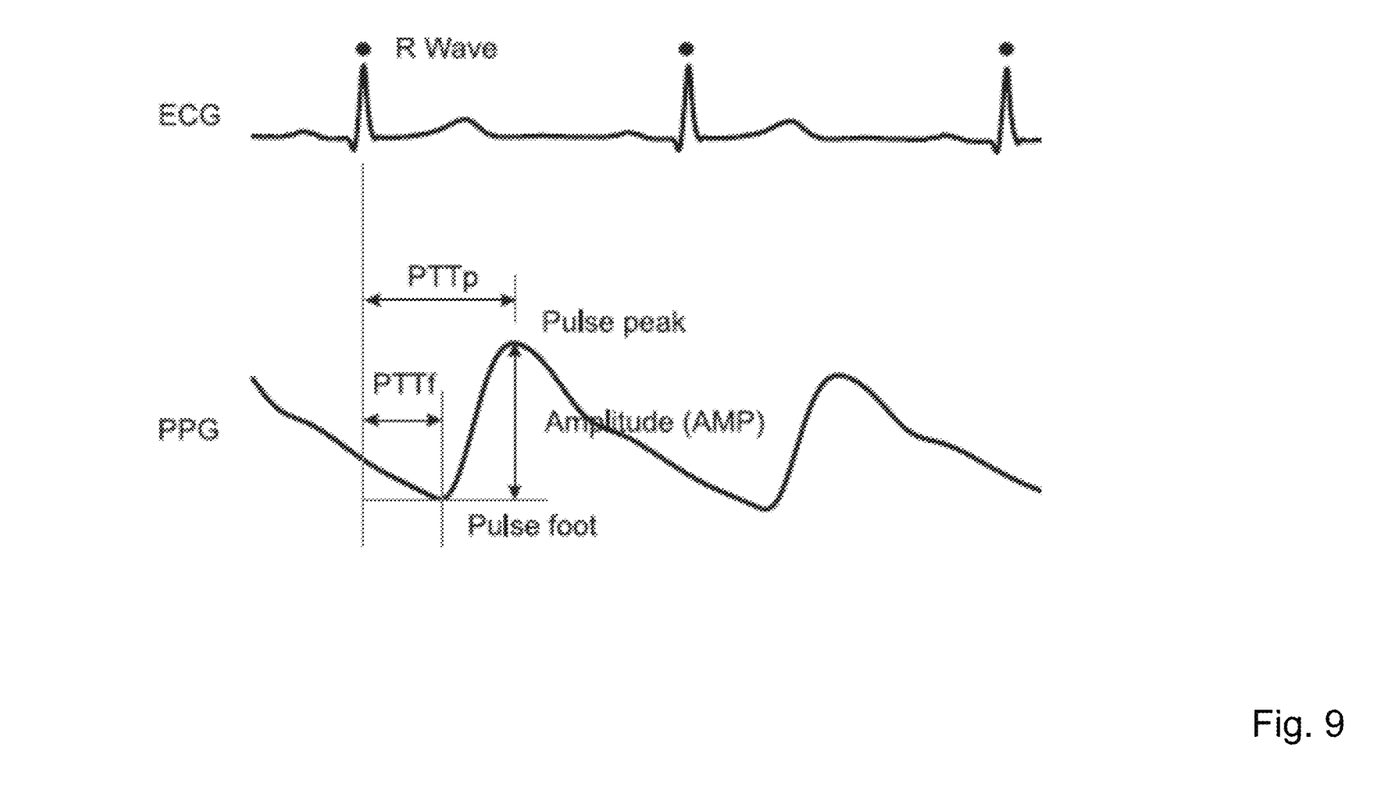
FIG. 9: an ECG signal and another PPG curve.

In general, the PTT can be computed from the ECG R-peak to PPG-foot or PPG-peak or another characteristic point of a PPG curve. Details concerning the determination of the PTT are visualized in FIGS. 8 and 9. FIG. 8 shows an ECG signal and a corresponding PPG curve. For each heart/pulse cycle, the PTT is calculated as the time difference between the R-wave in the ECG and the pulse foot of the PPG. Only if the heart rates taken from the ECG and from the PPG curve match, the PTT is completed. In FIG. 9, it is visualized that it is possible to define the PTT as a time between the R-wave in the ECG and the pulse foot of the PPG (so-called PTTf) and that it is possible to define the PTT as a time between the R-wave in the ECG and the pulse peak of the PPG (so-called PTTp).

While the normalization of PTT can be performed using data fitted across different users (varying heights and conditions of measurement), it can also be performed during an initialization phase specific to each user. In one embodiment of the disclosure, the user is first prompted to place the monitoring device at one location first (for example the chest) and PTT measurements are performed over a small time window (such as 1 minute) at this location. Then, the user is prompted to place the monitoring device at another location (for example the upper arm) and measurement is performed for the same time window there. Then, with the two PTTs computed, the normalization co-efficient can be computed by dividing one PTT by the other. Then, whenever the monitoring device is used at a location for measuring the vital signs, the normalization co-efficient can be used to get a uniform PTT irrespective of the location.

Figure 10:
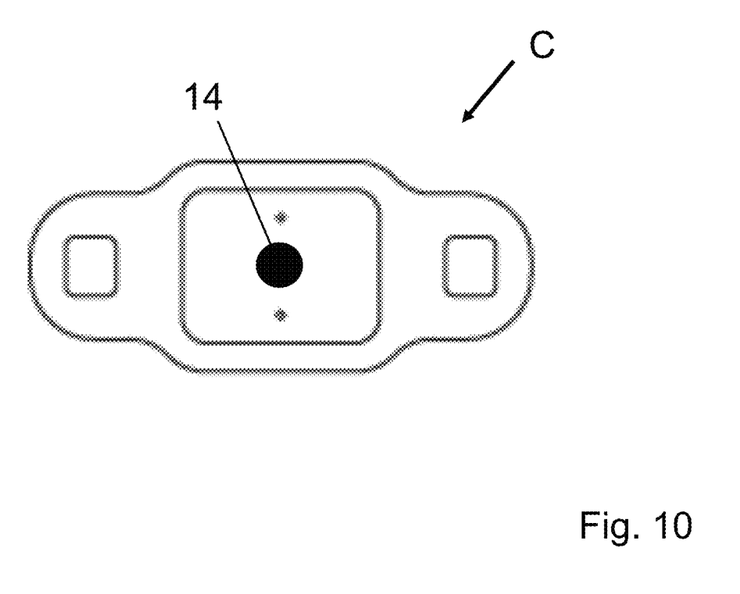
FIG. 10: a schematic view of a carrying means (patch) according to the disclosure, wherein the patch comprises an external electrode to be touched by the user.

FIG. 10 shows a schematic rear view of a carrying means C according to the disclosure. The carrying means C has the form of a patch, wherein the patch comprises an external electrode 14 to be touched by the user. The typical use of this external electrode 14 is as follows: the monitoring means, i.e. a carrying means C with a monitoring device D mounted therein, is placed on the arm or wrist of one hand of the wearer, e.g. a patient. The carrying means C comprises an electrode contact pad that is electrically connected to one electrode pin of the monitoring device D (this is not shown in FIG. 10 because the patch is shown in a rear view). The second electrode pin of the monitoring device D is connected to the external electrode 14. This external electrode 14 can be touched by the wearer using the other hand, thereby measuring the electrical activity across the chest between the electrode contact pad touching the arm or wrist and the external electrode 14 being touched by the other hand. Such a monitoring means typically continuously performs monitoring of body functions, e.g. computing of the heart rate or oxygen saturation or the ECG acquisition on the arm. It carries out an ECG measurement across the chest when the user touches the external electrode 14 with his other hand, i.e. the hand on which the monitoring means is not worn. In a typical embodiment, the monitoring device D mounted in the carrying means C creates an alert when any of the monitored body functions go beyond respective pre-defined thresholds and incites the user to touch the external electrode 14 with the other hand. Like this, the monitoring device D can measure an ECG that goes across the chest, i.e., between the electrode contact pad touching the arm or wrist at the location where the monitoring device is attached and the external electrode 14 being touched by the other hand.

In a typical embodiment, the external electrode 14 on the carrying means is in the shape of a graphic which can be a logo, for example a trademark of a company that sells the monitoring means or a logo of the monitoring means itself.

In a typical embodiment of the disclosure, the monitoring device comprises a temperature sensor to measure the skin temperature of a living organism wearing the monitoring device, wherein the temperature sensor comprises a pad for measuring the temperature on the same side of the monitoring device as the optical sensor. In typical embodiments, the pad is geometrically at least 5 mm away from the optical sensor. By keeping the pad away from the optical sensor, the heat generated due to the optical sensor does not affect the temperature measurements significantly.

In a typical embodiment of the disclosure, the location of the monitoring device on the body and the height of the user is considered, so that the temperature measurement can be normalized, similar to the above-described PTT normalization. In a typical embodiment of the disclosure, the monitoring device comprises a temperature sensor to measure the skin temperature and/or a capability of recording the location of the placement of the monitoring device on the body and/or a capability of obtaining the height of the wearer and/or a capability of normalizing the temperature sensor measurement based on the location and height of the wearer.

In a typical embodiment of the disclosure, the radio module of the monitoring device is also configured to receive signals and the processor of the monitoring device is configured to cause the radio module to transmit at least one vital sign signal upon receipt of a signal received by the radio module.

In a typical embodiment of the disclosure, at least one of the electrode connection lines of the patch or band comprises at least one connector to which a separate electrode can be attached externally. Such an electrode can be disposable or re-usable, and can be of different colors or shapes. In a typical embodiment, all electrode connection lines of the carrying means C have at least one such connector.

In one embodiment of a method according to the disclosure, there are two electrode contact pads on the patch or band in electrical contact with a patient's skin, wherein the electrode contact pads are separated by less than 10 centimeters. Furthermore, the voltage differential between the two electrode contact pads is measured, and the resulting measurements are analyzed to determine the heart rate of the patient. In typical embodiments, the heart rate is reported.

In a typical embodiment of the disclosure, the monitoring device comprises multiple optical sensors comprising green, infra-red and red light emitting diodes for sending light into the body of the wearer and one or more photodetectors configured to detect the waveforms reflected back from the body.

In a typical embodiment of the disclosure, the carrying means comprises a conductive pad on the patch or band that is configured to be brought in contact with the skin of the wearer and is configured to be electrically connected to the monitoring device to measure the skin temperature of the wearer.

In a typical embodiment of the disclosure, the carrying means and/or the monitoring device comprises multiple conductive pads on the patch or band or the monitoring device. Each of these pads is configured to be brought in contact with the skin of the wearer to measure skin temperature of the wearer at multiple points and to be connected to the monitoring device. In a typical embodiment of a method according to the disclosure, the monitoring device computes the skin temperature as an average or median of the temperature measurements from the multiple pads.

In a typical embodiment of the disclosure, the monitoring device comprises a microphone and/or vibration sensor configured to be brought in contact with skin of the wearer. The monitoring device furthermore typically comprises a capability of obtaining the location of the placement of the monitoring device on the body and a capability for marking a sound measured as the heart sound of the wearer when the placement of the device is on the chest. In other words: when the location of the monitoring device on the body is taken as an input, the data of the microphone and/or vibration sensor is labelled as the heart sound of the wearer, if the location is "chest".

In a typical embodiment of the disclosure, the monitoring means comprises a vital-signs monitor device that can obtain multiple signals and parameters from one or more locations on a human body. The vital-signs monitor device comprises of at least two electrodes that can obtain the electrical activity of the human body, one or more optical sensors placed between the two electrodes, a processor that can process the electrical and optical waveforms, an inertial sensor that can track the physical movement (or activity) of the body region where the device is placed, a memory unit for storing the data and a radio module for communicating the data from the device. The processor periodically takes measurements from the electrodes, converts the measurement to vital sign signals, and causes the transmitter to transmit the vital sign signals. Typical embodiments of the vital-signs monitor device measure certain vital signs of a patient, which typically include heart rate, pulse rate, pulse transit time, blood pressure based on pulse transit time, skin temperature, and peripheral oxygen saturation (SpO2), on a regular basis (either continuous or intermittent) and compare these measurements to defined limits. In typical embodiments, the vital-signs monitor device is a monitoring device according to the disclosure.

In a typical method according to the disclosure, the two electrode contact pads that measure the electrical activity are placed fewer than 12 cm apart and the one or more optical sensor(s) is/are placed at mid distance between the two electrode contact pads.

In a typical method according to the disclosure, the monitoring device is attached to the body of a user using a re-usable and/or disposable band that can be attached to different parts of the body, such as the upper arm, wrist or chest. When the monitoring device is attached to the band, the band comprises conductive electrodes to obtain the electrical activity, and the device's electrode pins are attached to the band's conductive electrodes to achieve an electrical conduction between the device and the band. The electrodes on the band are based on conductive material (such as stainless steel/metal/carbon) to obtain the electrical activity.

In a typical method according to the disclosure, a measuring of a cardiac heart rate is carried out. The method includes placing two electrodes in electrical contact with a patient's skin with a separation of fewer than 12 centimeters, measuring the voltage differential between the two electrodes, analyzing the measurements to determine a heart rate, and reporting the heart rate. In typical embodiments, the electrodes are body connection lines according to the disclosure.

In typical embodiments of the disclosure, the monitoring device and/or the carrying means is configured to determine an ElectroEncepheloGram (EEG) to measure the user's brain activity. In typical embodiments, monitoring device and/or the carrying means is configured to determine an ElectroOculoGram (EOG) to measure the eye movement (such as blinking).

As already mentioned, when recording ECGs, it is important to quantify the nature of the noise in a particular data set. In some embodiments of the disclosure, the monitoring device comprises a memory which comprises code configured to analyze and/or quantify the nature of noise in a particular data set, especially an ECG data set.

In typical embodiments of the disclosure, the method for monitoring vital signs comprises detecting a noisy ECG. In one embodiment, the pulse rate over a time window is measured using the optical sensor, and if the heart rate computed from the ECG does not match the pulse rate, the ECG signal in the window is discarded as noisy.

In typical embodiments of the disclosure, if the pulse rate and heart rate do not match, the pulse waveform is discarded as noisy.

In typical embodiments of the disclosure, the location of use of the monitoring device is taken as input (taking values such as "arm" or "chest"), and when the heart rate and pulse rate do not match, the ECG signal in the window is discarded as noisy when the device is used on the arm or wrist, and the pulse signal in the window is discarded in case the device is used on the chest.

In typical embodiments of a method according to the disclosure, the method comprises steps to differentiate between ECG signals and EMG signals. In typical embodiments of a method according to the disclosure, the method comprises steps to measure a PTT, which is a marker for blood pressure variations. The PTT can be used for tracking long term BP variations.

A desirable way to carry out a differentiation between ECG and EMG is as follows: The monitoring device measures the electrical activity, which can comprise the ECG and EMG signals. Then, the method differentiates between ECG signals that are contaminated with EMG signals and clean ECG signals. In typical embodiments, an accelerometer value over a window of measurement is checked to see if it exceeds a pre-defined threshold. If the accelerometer value exceeds the threshold, the electrical signal measured is defined as contaminated by an EMG signal. The accelerometer thresholds are typically set experimentally, after collecting data from different subjects at rest and when they are made to perform muscular activity (such as arm flex, chest push ups).

In another typical embodiment, the power spectrum of the electrical signal measured over a window is compared to a pre-defined threshold. If the spectrum exceeds the threshold, the electrical signal measured is defined as contaminated by EMG signal. During muscular activity, the power spectrum of EMG is significantly higher than in cases where no muscular activity occurs (when only ECG is present).

In another typical embodiment, the electrical signal and the accelerometer signal are first transformed into a different domain, such as the frequency or wavelet domains. During muscle activity, there is a corresponding activity measured on the accelerometer sensor as well, while the cardiac signal due to ECG has no impact on the measured accelerometer data. Thus, removing all significant components of the accelerometer from the electrical signal will remove the EMG and other movement induced noise sources as well. In one typical embodiment, to remove the EMG and noise sources, the frequency or wavelet components of the accelerometer are scaled and removed from the transformed electrical signal. After removing the components, the electrical signal is transformed back to the original time domain. The resulting signal is the ECG signal with noise sources removed. When this signal is subtracted from the original electrical signal (before any transformation), the resulting signal is the EMG signal possibly contaminated with movement noise sources.

In another typical embodiment, the ECG and EMG signals are separated from each other by filtering the signals and by using the pulse rate computed from the pulse signal. For a window of the measurement, the signal is first filtered using a narrow band pass filter at the frequency of the pulse rate measured from the pulse signal. The resulting filtered signal is the ECG signal. When the resulting filtered signal is filtered from the original signal, the remaining signal is the EMG signal.

In typical embodiments, the monitoring device is configured to measure a respiration rate. In typical embodiments, this is achieved using a microphone and/or a vibration sensor. In typical embodiments, the monitoring device comprises other sensors such as an accelerometer, temperature sensor and/or oxygen saturation sensor to measure other characteristics associated with the patient. These other sensors may be internal to the monitoring device or to the carrying means or may be external sensors that are operably connected to the monitoring device and/or the carrying means, e.g., via a wireless connection.

In typical embodiments, the monitoring device and/or the components of the carrying means are encapsulated such that the patients wearing the monitoring means can bathe or shower and engage in their normal activities without degradation of the function of the monitoring means, i.e. a combination of a monitoring device according to the disclosure and a carrying means according to the disclosure, e.g., a patch.

In typical embodiments, the line connection pins and/or the body connection lines and/or the electrode contact pads are gel electrodes, which typically comprise a hydrogel material that is conductive and has low contact impedance on the skin when compared to using a metal electrode. In case these components are metal electrodes, they typically comprise a Stainless Steel (such as medical grade 316L or a bio-compatible 304 grade). In typical embodiments, a combination of metal and/or hydrogel and/or conductive ink and or any other material disclosed above is used as electrode material for the line connection pins and/or the body connection lines and/or the electrode contact pads.

The application of the disclosure is broad and ranges from homes, clinics, ambulances, nursing homes, sports, and public arenas, to medical centers.

One important result of the disclosure is a monitoring device that can acquire several parameters from a single physical location on the body. This monitoring device comprises an innovative placement of sensors on the different parts of the device to allow for seamless acquisition of different signals from the single location.

The monitoring device is attachable to a patch to create a monitoring means that can simultaneously measure optical signals and electrical signals. The patch can be attached to different locations on the body, and depending on the location can determine the type and quality of the signals. The monitoring means can carry out methods to distinguish ECG signals from EMG signals depending on the location of the body and the time differences between optical and electrical signal waveforms.

It is pointed out that the methods presented in this specification, especially the methods for differentiating between a clean ECG signal and a combined ECG/EMG signal, do not necessarily need a monitoring device according to the disclosure for being carried out. For example, the differentiation between a clean ECG signal and a combined ECG/EMG signal does not require an optical sensor configured to carry out PPG measurements.

The disclosure is not limited to the embodiments described here. The scope of protection is defined by the claims.

Furthermore, the following claims are hereby incorporated into the Detailed Description, where each claim may stand on its own as a separate embodiment. While each claim may stand on its own as a separate embodiment, it is to be noted that—although a dependent claim may refer in the claims to a specific combination with one or more other claims—other embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having capability of performing each of the respective acts of these methods.

REFERENCE LIST

1 Casing
2 Back side of monitoring device
3.1, 3.2 Electrode pins
4 Front side of monitoring device
5 Optical sensor
6 Housing
7.1, 7.2 Contact pad housings
8.1, 8.2 Electrode contact pads
9.1, 9.2 Body connection lines
10.1, 10.2 Line connection pins
11 Flap
12 View opening for optical sensor
13 Additional opening
14 External electrode
C Carrying means
D Monitoring device
M Monitoring means
P Patient

The invention claimed is:

1. A method for monitoring of vital signs of a living organism using a monitoring device, wherein the method comprises:
receiving a first electrical activity of the living organism using at least two electrode pins;
sensing a pulse of the living organism using an optical sensor;
determining whether the first electrical activity is a clean ECG signal or a combination of an ECG signal and an EMG signal;
measuring a time-dependent accelerometer waveform and a time-dependent waveform of the first electrical activity concurrently;
computing a mean of the accelerometer waveform on a pre-defined time window;
removing the mean from the accelerometer waveform over the time window so as to create a residual accelerometer signal;
checking if a sum or a root mean square (RMS) of the residual accelerometer signal exceeds a pre-defined signal threshold; and
labeling the first electrical activity as the clean ECG signal when the sum or the RMS of the residual accelerometer signal does not exceed the pre-defined signal threshold and labeling the first electrical activity as the combination of the ECG signal and the EMG signal when the sum or the RMS of the residual accelerometer signal exceeds the pre-defined signal threshold.

2. The method of claim 1, wherein the determining comprises:
based on determining that the first electrical activity is labelled as the combination of the ECG signal and the EMG signal, transforming the accelerometer and electrical activity waveforms into frequency domains;
removing frequency components of the transformed accelerometer waveform from frequency components of the first electrical activity;
constructing a second electrical activity after removing the frequency components into time domain, with the resulting signal labelled as the ECG signal; and
subtracting the ECG signal from the first electrical activity and labelling the resulting signal as the EMG signal.

3. The method of claim 1, wherein the determining further comprises:
based on determining that the electrical activity is labelled as the combination of the ECG signal and the EMG signal, transforming the accelerometer and electrical activity waveforms into wavelet domains;
removing wavelet components of the transformed accelerometer signal from wavelet components of the first electrical activity;
constructing a second electrical activity after removing the wavelet components into time domain, with the resulting signal labelled as the ECG signal; and
subtracting the ECG signal from the first electrical activity and labelling the resulting signal as the EMG signal.

4. A method for monitoring of vital signs of a living organism using a monitoring device, wherein the method comprises:
receiving a first electrical activity of the living organism using at least two electrode pins;
sensing a pulse of the living organism using an optical sensor;
determining whether the first electrical activity is a clean ECG signal or a combination of an ECG signal and an EMG signal;
measuring a time-dependent accelerometer waveform and a time-dependent waveform of the first electrical activity concurrently;
computing a mean of the accelerometer waveform on a pre-defined time window;
removing the mean from the accelerometer waveform over the time window so as to create a residual accelerometer signal;
determining a power spectrum of the residual accelerometer signal;
checking if a maximum amplitude of the power spectrum at any frequency exceeds a pre-defined power threshold; and
labeling the first electrical activity as the clean ECG signal when the maximum amplitude does not exceed the pre-defined power threshold and labeling the first electrical activity as the combination of the ECG signal and the EMG signal when the maximum amplitude exceeds the pre-defined power threshold.

5. The method according to claim 4, wherein the determining comprises:
based on determining that the first electrical activity is labelled as the combination of the ECG signal and the EMG signal, transforming the accelerometer and electrical activity waveforms into frequency domains;
removing frequency components of the transformed accelerometer waveform from frequency components of the first electrical activity;
constructing a second electrical activity after removing the frequency components into time domain, with the resulting signal labelled as the ECG signal; and
subtracting the ECG signal from the first electrical activity and labelling the resulting signal as the EMG signal.

6. The method according to claim 4, wherein the determining comprises:
based on determining that the electrical activity is labelled as the combination of the ECG signal and the EMG signal, transforming the accelerometer and electrical activity waveforms into wavelet domains;
removing wavelet components of the transformed accelerometer signal from wavelet components of the first electrical activity;
constructing a second electrical activity after removing the wavelet components into time domain, with the resulting signal labelled as the ECG signal; and
subtracting the ECG signal from the first electrical activity and labelling the resulting signal as the EMG signal.

7. A method for monitoring of vital signs of a living organism using a monitoring device, wherein the method comprises:
receiving a first electrical activity of the living organism using at least two electrode pins;
sensing a pulse of the living organism using an optical sensor;
computing a heart rate in a rate time window from the first electrical activity;
computing a pulse rate from the pulse sensed by the optical sensor in the rate time window;
obtaining a position of a placement of the monitoring device on the body, wherein the position has one of the position values "arm" or "wrist" or "chest";
discarding the first electrical activity as noisy when the computed heart rate does not match the computed pulse rate and when the position of the monitoring device on the body has the position value "arm" or "wrist"; and
discarding the pulse as noisy when the computed heart rate does not match the computed pulse rate and when the position of the monitoring device on the body has the position value "chest".

8. A method for monitoring of vital signs of a living organism using a monitoring device, wherein the method comprises:
receiving a first electrical activity of the living organism using at least two electrode pins;
sensing a pulse of the living organism using an optical sensor;
determining a Pulse Travel Time (PTT) based on the first electrical activity and the pulse; and
checking whether the PTT is noisy, wherein the PTT computed over a PTT-window of measurement is discarded as noisy when an EMG signal is present, when the heart rate does not match to the pulse rate, or when noise is present in either an ECG signal or the pulse.

* * * * *